United States Patent [19]
Andrulis, Jr. et al.

[11] Patent Number: 6,001,828
[45] Date of Patent: Dec. 14, 1999

[54] USE OF TUMOR FACTOR INHIBITORS TOGETHER WITH ANTIVIRAL AGENTS AND THERAPEUTIC COMPOSITIONS THEREOF AGAINST HIV INFECTION

[76] Inventors: Peter Andrulis, Jr., 7220 Armat Dr., Bethesda, Md. 20817; Isaac A. Angres, 6 War Admiral Ct., Gaithersburg, Md. 20878

[21] Appl. No.: 08/956,277

[22] Filed: Oct. 23, 1997

Related U.S. Application Data

[63] Continuation of application No. 08/462,034, Jun. 5, 1995, abandoned, which is a continuation of application No. 08/101,752, Aug. 4, 1995, abandoned.

[51] Int. Cl.$^6$ .......................... A61K 31/55; A61K 31/445
[52] U.S. Cl. ............................................. 514/221; 514/323
[58] Field of Search ...................................... 514/221, 323

[56] References Cited

U.S. PATENT DOCUMENTS 5,641,773  6/1997  Pardee et al. ........................... 514/221

OTHER PUBLICATIONS

Makonkawkeyoon et al., Proc. Natl. Acad. Sci. USA (1993), 90(13), 5974–8 (Abstract Only).

*Primary Examiner*—Jerome D. Goldberg
*Attorney, Agent, or Firm*—Isaac Angres

[57] ABSTRACT

A pharmaceutical composition comprising: (a) a tumor necrosis factor inhibitor; (b) a compound selected from the group consisting of reverse transcriptase inhibitors, protease inhibitor, a gene inhibitor, myristoylation inhibitors, cell-virus binding inhibitors, LTR promoter site inhibitors, ribosome inactivators, platelet aggregation inhibitors and prophylactic and therapeutic HIV vaccines, and (c) a pharmaceutical inert nontoxic carrier are described.

1 Claim, No Drawings

USE OF TUMOR FACTOR INHIBITORS TOGETHER WITH ANTIVIRAL AGENTS AND THERAPEUTIC COMPOSITIONS THEREOF AGAINST HIV INFECTION

This application is a continuation of application Ser. No. 08/462,034 filed Jun. 5, 1995 which appliction is now: abandoned which is a continuation of Ser. No. 08/101,752, filed Aug. 4, 1995, which application is now abandoned.

The present invention relates to de novo compositions of matter for the treatment of AIDS. The present invention further relates to the de novo compositions of matter containing TNF inhibitors and antiviral agents selected from the group of reverse transcriptase inhibitors, protease inhibitors, gene inhibitors (of such genes as gag, env, tat, rev, and pol), myristoylation inhibitors, cell-virus binding inhibitors, LTR promoter site inhibitors, ribosome inactivators, platelet aggregation inhibitors and prophylactic and therapeutic HIV vaccines.

Description of the Prior Art

Under ideal circumstances, a drug should give a patient a lasting cure, or at least improve the condition of the patient having a particular disease while causing minimal side effects. Latest advances in drug research rely on the systematic research and further understanding of the disease process at the molecular level. Over the last few years there has been an enormous amount of research directed toward Human Immunodeficiency Virus (HIV), which causes Acquired Immunodeficiency Syndrome (AIDS). At the present time, the most widely accepted therapeutic composition for treating AIDS is the compound azidothymidine, also known as AZT. Recent discoveries relating to AIDS have implicated tumor necrosis factor as a stimulatory agent in the growth of HIV. Because tumor necrosis factor has been implicated as a factor in AIDS, there has been a need to look at tumor necrosis factor inhibitors of those diseases. Tumor necrosis factor inhibitors which have been studied in the past include thalidomide, pentoxifylline and xanthine derivatives.

Within the context of the present specification, when applicant refers to tumor necrosis factor (TNF) it is meant to signify TNF-$\mu$, TNF -p or mixtures thereof. Antiviral therapy such as therapy for Human Immunodeficiency Virus, is the subject of vigorous research all over the world. Viruses are basically subcellular particles that can live only as intracellular parasites. They basically consist of a genome of RNA or DNA (single or double stranded), packaged inside a protein, and in some cases, with a lipid envelope covering the whole particle. Additionally, these particles infect cells, and replicate within the infected cell using much of the host cell apparatus needed to synthesize macromolecules (e.g., DNA, RNA, protein). A large number of progeny then leave the cell, often by causing it to burst. The viral progeny then infect other cells and these processes repeat over and over again. Because HIV shares many host functions for replication, the possibility of interfering with his life cycle was initially considered remote. But proteins specific to the functioning of the virus have now been identified. At the present level of research, it is possible to design molecules which interfere with these viral functions with acceptable or bearable toxic side effects. Because of the recent implications of tumor necrosis factor in the development of HIV-1, it would appear desirable to combine therapeutic methods wherein a TNF inhibitor is administered to a patient with other pharmaceutical compounds such as reverse transcriptase inhibitors, gene inhibitors, and HIV protease inhibitors, myristoylation inhibitors, cell-virus binding inhibitors, LTR promoter site inhibitors, LTR promoter site inhibitors, ribosome inactivators, platelet aggregation inhibitors and prophylactic and therapeutic HIV vaccines.

Thalidomide was first synthesized and marketed in the 1950's as a sedative. The toxicity of the compound was so low that a dose killing 50% of animals ($LD_{50}$) could not be established. Thalidomide was therefore thought to be a safer alternative to barbiturates. In 1961, thalidomide administered to pregnant women resulted in an epidemic of congenital malformations. The incidence of malformed babies paralleled the sales of thalidomide and quickly dropped off when thalidomide was removed from the market.

Oral administration of thalidomide in the range of 100–200 mg in adult humans results in a peak blood level of 0.9–1.5 mg/liter after 4–6 hours. Hydrolytic cleavage of thalidomide occurs In vitro, the rate of which increases as the pH increases. However, hydrolytic cleavage of thalidomide in serum at pH 7.4 is much slower than in vitro at pH 7.4. This may be due to thalidomide being highly bound to plasma proteins. Studies in animals demonstrated high thalidomide concentrations in the gastrointestinal tract, liver and kidneys with lower concentration in muscle, brain and adipose tissue. In pregnant animals, thalidomide can pass across the placenta.

Although a complete study of thalidomide metabolism in humans has not been performed, in animals the main pathway for thalidomide breakdown appears to be nonenzymatic hydrolytic cleavage. Even though immunomodulatory effects of thalidomide have not been clearly defined at the molecular, thalidomide has been used as single therapeutic agent or in combination therapy to treat a number of immunologic and inflammatory diseases such as aphthous ulcers (Jenkins et al., 1984; Grinspan, 1985; Revuz et al., 1990), Graft vs Host Disease (Lim et al., 1988; McCarthy et al., 1988; Henley et al., 1988), erythema nodosum leprosum (Sheskin, 1965; Sheskin and Convft, 1969; Pearson and Vedagiri, 1969), Behcets Syndrome (Saylan and Saltik, 1982; Jorizzo et al., 1986), actinic prurigo (Londono, 1973; Lowell et al., 1983), ulcerative colitis (Waters et al., 1979) and discoid lupus erythematosus (Knop et al., 1981). Most of these diseases are associated with elevated levels of such cytokines as TNF-alpha, IL-1 beta, IL-6 and/or IL-8 among others. Thalidomide has a proven ability to suppress production and/or activity of cytokines which will prove useful in ameliorating or eliminating the inflammation and/or repression of antigen expression associated with chronic hepatitis.

In the above studies, dosages ranging from 100 mg/day to 800 mg/day were administered without serious side effects.

The prior art is silent regarding compositions of matter and uses which include tumor necrosis factor inhibitors together with anti-AIDS agents, reverse transcriptase inhibitors, HIV protease inhibitors, gene inhibitors, myristoylation inhibitors, cell-virus binding inhibitors, LTR promoter site inhibitors, LTR promoter site inhibitors, ribosome inactivators, platelet aggregation inhibitors and prophylactic and therapeutic HIV vaccines and in combined formulations therewith.

Thalidomide has been shown to inhibit TNF-alpha production in erythema nodosum leprosum patients (Samo et al., 1991) and in vitro stimulated monocytes (Sampaio et al., J. Exp. Med., 173:699–703, 1991). Shannon et al. (Amer. Soc. for Microbiology Ann. Meeting, Abst. U-53, 1990) indicated thalidomide inhibited IL-1 beta production in vitro. In light of thalidomide inhibitory activity on IL-1 beta, TNF-alpha and bFGF the purpose of this invention is to use thalidomide alone or in combination with other anti-HIV therapeutic agents to treat HIV infection.

SUMMARY OF THE INVENTION

The primary objects of the present invention are to provide pharmaceutical compositions containing a tumor necrosis factor inhibitor and an HIV reverse transcriptase inhibitor and to administer both independently.

Another object of the present invention is to provide pharmaceutical compositions containing a tumor necrosis factor inhibitor and a HIV protease inhibitor.

An additional object of the present invention is to provide compositions of matter comprising a tumor necrosis factor inhibitor and an HIV gene inhibitor.

Still another object of the present invention is to provide compositions of matter comprising tumor necrosis factor inhibitors and non-nucleoside reverse transcriptase inhibitors.

A further object of the present invention is a method for the therapeutic treatment of HIV infections by administering concurrently a combination of a tumor necrosis factor inhibitor and one or more compounds selected from the group consisting of reverse transcriptase inhibitors, HIV protease inhibitors, gene inhibitors, myristoylation inhibitors, cell-virus binding inhibitors, LTR promoter site inhibitors, ribosome inactivators, platelet aggregation inhibitors and prophylactic and therapeutic HIV vaccines.

DESCRIPTION OF THE PREFERRED EMBODIMENT

The present invention deals with compositions of matter useful for therapeutic treatment of HIV and being a combination of tumor necrosis factor inhibitors and a compound selected from the group consisting of reverse transcriptase inhibitors, HIV protease inhibitors, gene inhibitors, myristoylation inhibitors, cell-virus binding inhibitors, LTR promoter site inhibitors, ribosome inactivators, platelet aggregation inhibitors and prophylactic and therapeutic HIV vaccines.

The preferred compounds which are used as tumor necrosis factor inhibitors are thalidomide, pentoxifylline, and xanthine derivatives.

Some of the preferred reverse transcriptase inhibitors include azidothymidine (AZT), dideoxy inosine (ddI), dideoxycytidine (ddc), fluorodideoxythymidine (FddT), as well as other compounds such as D4T, FddT 3TC, BI-RG-587, R-82150 and L697639 whose structures are shown below.

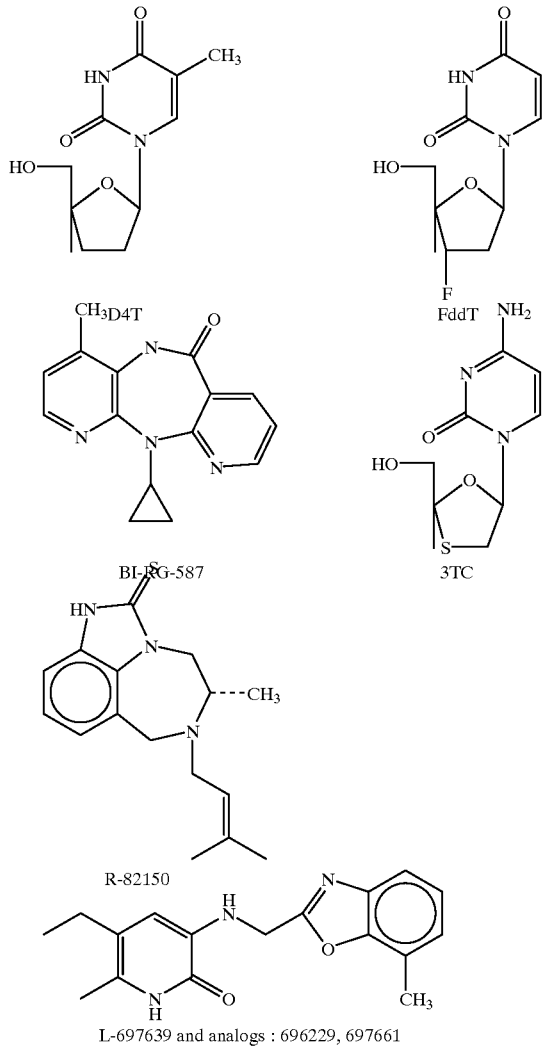

Other reverse transcriptase inhibitors include:

Lipophilic prodrug of AZT

Bisheteroaryl/piperazine U88Z04E

Some of the preferred HIV-protease inhibitors which can be used as part of this invention are described structurally below.

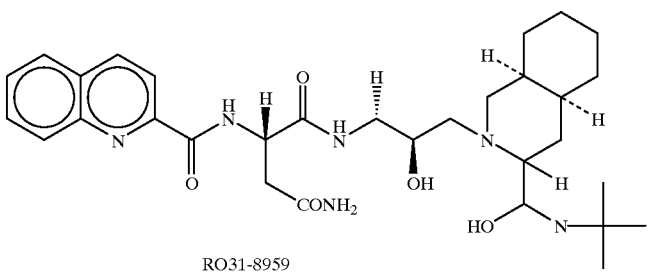

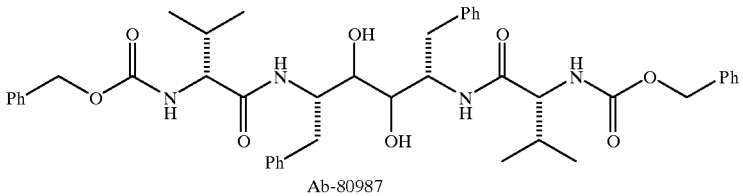

Ab-80987

KN1-227 and KN1-272-transition state mimetic tdipeptides

SC52151

The preferred compounds which would act as gene inhibitors would be benzodiazepine derivatives. One promising agent which inhibits the tat gene is RO-24-7429 which is a benzodiazepine shown below.

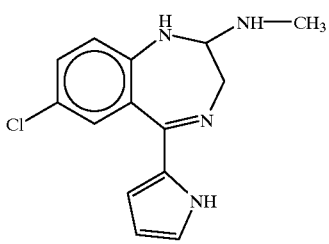

RO-24-7429 and RO5-3335 analog (tat)

Further inhibitors include:

TAR antisense transcript encoded in adeno-associated virus expression vector (tat)

Mutant HIV expression vector (rev)

The preferred inhibitors of myristoylation would be:

AC2, a synthetic phospholipid

The preferred inhibitors of cell-virus binding include:

EL, a synthetic amino derivative of ether phospholipids

Recombinant gp120+MF59 adjuvant vaccine

Recombinant gp160+MF59/MTP-PE adjuvant vaccine

Recombinant soluble CD4 gp120 peptide-PPD

The preferred inhibitors of LTR promotor sites would include:

Ÿ Triplex-forming oligonucleotide

Ÿ Strand 3B of triplex forming oligonucleotide

The preferred inhibitors of platelet aggregation would include:

Dipyridamole

The preferred ribosome inactivators would include:

GLQ223-purified trichosanthin

The preferred prophylactic and therapeutic HIV vaccines would be:

recombinant gp120+MF59 adjuvant vaccine recombinant gp160+MF59/MTP-PE vaccine recombinant gp 160 vaccine gp120 peptide-PPD Therapeutically, the present invention presents a method of treating HIV by combination therapy which includes administering a tumor necrosis factor inhibitor and, independently, a compound selected from the group of reverse transcriptase inhibitors, HIV protease inhibitors, gene inhibitors, myristoylation inhibitors, cell-virus binding inhibitors, LTR promoter site inhibitors, ribosome inactivators, platelet aggregation inhibitors, platelet aggregation inhibitors and prophylactic and therapeutic HIV vaccines.

The therapeutically-effective amounts of thalidomide are typically 30 mg to 1500 mg and preferably 200 mg to 500 mg.

When thalidomide is used in combination with other drugs effective in the treatment of HIV infection, the amount of thalidomide is typically in the range of about 30 mg to about 1000 mg while the other drugs are present in the range of about 10 mg to 500 mg. For example, an effective combination for treating HIV infection is a gelatin capsule containing 200 mg of thalidomide and 200 mg of AZT given three times daily. Two capsules each containing the active ingredient may also be prescribed.

The precise amount of thalidomide alone or with the other active materials mentioned above will vary depending, for example, on the condition for which the drug is administered and the size and kind of the mammal. Generally speaking, the thalidomide can be employed in any amount effective in the treatment of HIV infection. The symptoms of the above conditions generally are improved.

For humans, typical effective amounts of thalidomide for use in the unit dose compositions of the present invention range from about 30 mg to 1500 mg per 24 hours; however, greater amounts may be employed, if desired. This range is based on administration to a 70 kg human. A preferred amount is 200 mg to 500 mg. The more preferred range contains about 200 mg to 500 mg of thalidomide per 24 hours.

As mentioned above, thalidomide may be given alone or in combination with other drugs which are also useful in the treatment of HIV infection. For example, when thalidomide is used with a reverse transcriptase inhibitor a typical formulation contains from about 100 mg to 500 mg of thalidomide and from about 150 mg to 400 mg of AZT. The formulations are administered over a 24 hour period.

The compound present invention can be prepared and administered in a wide variety of oral and parenteral dosage forms. It will be obvious to those skilled in the art that the following dosage forms may comprise as the active component, either thalidomide alone or in combination with other compounds.

Preferably the compounds of the present invention are administered orally, intramuscularly, subcutaneously or intravenously.

For preparing pharmaceutical compositions from the compounds of the present invention, pharmaceutically-acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders, capsules and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it.

Similarly, cachets and lozenges are included. Tablets, powders, capsules, pills, cachets, and lozenges can be used as solid dosages forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool and thereby to solidify.

Liquid form preparation-include solutions, suspensions, and emulsions, for example, water or water propylene glycol solutions. For parenteral injection, liquid preparations can be formulated in solution in aqueous polyethylene glycol solution.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparation which are intended to be converted, shortly before use, to liquid form preparation for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

It is also possible to administer thalidomide in a time-release formulation. A wide variety of methods are now available in the art for preparing time-release or long-acting compositions. Any of these time-release or long-acting formulations are suitable in the practice of the present invention as long as it does not adversely affect the effectiveness of the thalidomide in the treatment of HIV infection.

Advantages of time-release formulations include a lower concentration of peak serum absorption which substantially reduces the adverse side effects and toxicity of the compound administered. In addition, a reduced frequency of administration results, which substantially improves patient compliance.

A frequency of administration of every 12 or 24 hours would be preferred. In addition, more constant serum concentration of thalidomide would result thereby allowing a more consistent relief of symptoms.

The following examples, not to be construed as limiting, illustrate formulations which can be made according to the invention.

The following preferred examples are described below. However, they are representative without departing from the spirit of the invention or scope of the subject matter.

EXAMPLE 1

200 milligrams of thalidomide are mixed with 400 milligrams of AZT. The active ingredients are triturated and Q.S. with lactose to selected capsule size.

EXAMPLE 2

200 milligrams of thalidomide are mixed with 500 milligrams of ddl. The active ingredients are triturated and Q.S. with lactose to selected capsule size.

EXAMPLE 3

300 milligrams of thalidomide are mixed with 500 milligrams of ddc. The active ingredients are triturated and Q.S. with lactose to selected capsule size.

EXAMPLE 4

200 milligrams of pentoxifylline are mixed with 500 milligrams of AZT. The active ingredients are triturated and Q.S. with lactose to selected capsule size.

EXAMPLE 5

300 milligrams of pentoxifylline are mixed with 500 milligrams of DDI. The active ingredients are triturated and Q.S. with lactose to selected capsule size.

The foregoing description is offered primarily for purposes of illustration. It will be readily apparent to those skilled in the art that numerous variations in both the formulations and their method of use, not mentioned above, may be made without departing from the spirit and scope of the invention.

What is claimed is:

1. An enhanced pharmaceutical composition comprising: (a) an enhanced effective amount of thalidomide; (b) an effective amount of a compound having the formula

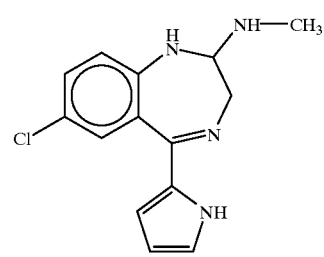

RO-24-7429 and (c) a pharmaceutical inert nontoxic carrier.

* * * * *